(12) United States Patent
Ternes (10) Patent No.: US 7,016,730 B2
(45) Date of Patent: Mar. 21, 2006

(54) METHOD OF OPERATING IMPLANTABLE MEDICAL DEVICES TO PROLONG BATTERY LIFE

(75) Inventor: David J. Ternes, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 572 days.

(21) Appl. No.: 10/295,099

(22) Filed: Nov. 15, 2002

(65) Prior Publication Data

US 2004/0098060 A1 May 20, 2004

(51) Int. Cl.
*A61N 1/365* (2006.01)

(52) U.S. Cl. .............................. 607/17; 607/14; 607/16; 607/19

(58) Field of Classification Search .................. 607/16, 607/19, 18, 17, 24

See application file for complete search history.

(56) References Cited

U.S. PATENT DOCUMENTS

| | | | |
|---|---|---|---|
| 4,860,751 A | | 8/1989 | Callaghan |
| 5,376,106 A | * | 12/1994 | Stahmann et al. ............. 607/18 |
| 5,766,228 A | * | 6/1998 | Bonnet et al. ................. 607/16 |
| 6,076,015 A | | 6/2000 | Hartley et al. |
| 6,363,280 B1 | * | 3/2002 | Mouchawar et al. .......... 607/16 |

* cited by examiner

*Primary Examiner*—Kennedy Schaetzle
*Assistant Examiner*—Joy Patel
(74) *Attorney, Agent, or Firm*—Nikolai & Mersereau, P.A.; Thomas J. Nikolai (57) ABSTRACT

A method of conserving power and extending the life of a battery in an implantable rate-responsive cardiac rhythm management device. In accordance with the preferred embodiment, a first physiologic sensor is used to enable a power consuming feature only when the first sensor produces an output falling within a predetermined range and subsequently disables the power consuming feature when the output of the first sensor falls back outside the predetermined range. The first sensor may measure heart rate, physical movement, posture or other parameters and the power consuming feature may comprise further physiologic sensors, a different mode of pacing or a combination thereof.

31 Claims, 8 Drawing Sheets

METHOD OF OPERATING IMPLANTABLE MEDICAL DEVICES TO PROLONG BATTERY LIFE

BACKGROUND OF THE INVENTION

I. Field of the Invention

This invention relates generally to battery-powered, implantable medical devices, and more particularly to a method of operating such medical devices in a way that conserves battery power and thereby prolongs the operating life of the implantable device.

II. Discussion of the Prior Art

A number of different implantable medical devices are used to provide electrical stimulation to target tissue. While the present invention will be described in the context of implantable cardiac rhythm management devices, the present invention is not to be limited to that particular application, but may find use in neural stimulators, implantable drug delivery devices, etc.

Cardiac rhythm management devices include bradycardia pacemakers, anti-tachycardia pacemakers and implantable automatic defibrillators. Each of these devices includes one or more sensors for detecting cardiac depolarization signals. Included may be both atrial and ventricular sense amplifiers that are connected to provide inputs to a microprocessor-based controller. The microprocessor-based controller, operating under control of a program is designed to control the time at which a pulse generator is activated to deliver cardiac stimulating pulses to target tissue in one or both ventricles, or in the case of DDD pacemakers, to atrial tissue as well. In addition to sensors for detecting cardiac depolarization signals, in a class of stimulators referred to as "rate adaptive", the devices may include one or more additional sensors for detecting physiologic parameters of the patient and for providing inputs to the microprocessor-based controller for adjusting the rate at which cardiac pacing pulses are delivered to meet physiologic demand.

The sensing circuits as well as the microprocessor-based controller and the pulse generator are power consuming devices and, generally speaking, receive their power from a DC battery contained within the housing of the implantable device. Great strides have been made over the past several years in battery designs to lengthen the time between an implant and when it becomes necessary to explant the device and replace it with another. In addition to improvements in battery chemistry, implantable medical devices, such as pacemakers and implantable defibrillators, have also been programmed in a way to conserve battery power. For example, programs have been written such that selected circuits are put in a "sleep mode" which is a low power consuming state, until such time as an event occurs to "awaken" the circuitry so that it can function in its intended mode.

Rate responsive pacemakers have been devised that incorporate multiple sensors for measuring physiologic demand and for developing a control signal for the microprocessor based controller that constitutes a blend of the outputs from the multiple sensors. For example, rate responsive pacemakers may incorporate an accelerometer for detecting patient movement and a minute ventilation sensor for detecting respiratory activity as an indicator of physiologic demand. When a patient having such a pacemaker implanted goes from a resting state to a minimal level of activity, the accelerometer is the primary rate controlling signal source. As activity level increases and the body requires a greater blood supply, respiratory activity becomes an important measure of physiologic demand. A discussion of rate adaptive pacemakers having multiple sensors is contained in the Stahmann et al. U.S. Pat. No. 5,376,106 and its disclosure is hereby incorporated by reference.

The Callaghan U.S. Pat. No. 4,860,751 describes an arrangement having a power consuming sensor for measuring the partial pressure of oxygen in the blood, a parameter that is known to vary with exercise. To conserve power, that sensor is disabled when a person is at rest. A passive, piezoelectric sensor is provided for turning on power to the $PO_2$ sensor when activity produces an output above a predetermined threshold. It is to be especially noted, however, that in the Callaghan '751 patent only the $PO_2$ sensor is operational upon being powered up. There is no blending of the multiple sensors in arriving at the control signal for varying the stimulation pulse rate of the device.

In accordance with the present invention, in order to conserve power, one or more activity sensors is/are enabled based on the activity of a single sensor when the activity measured by the first sensor falls into a predetermined range. The microprocessor is made to execute a blending algorithm, which combines the outputs of the multiple sensors in a prescribed way to produce the delta rate control signal. Further, in accordance with the present invention, those additional sensors are disabled when the activity level measured by the single sensor or a combination of all sensors falls outside of the specified range.

It is also known that most patients' natural pacemakers, i.e., the sinus node, provides an adequate heart rate for producing a cardiac output satisfactory for low levels of exertion, but not for high levels of exertion. This is known as chronotropic incompetence. In accordance with the present invention, means are provided for determining the cross-over point for chronotropic incompetence, i.e., activity level where the device could be switched from tracking an intrinsic rate to being sensor-driven. Further, when the level of activity again drops, the device can disable the activity sensor so long as the intrinsic rate is in the range from a programmed lower rate limit to the cross-over point.

When it is considered that an average pacemaker patient spends in excess of 75% of time in sedentary activities, e.g., sleeping, watching T.V., etc., the need for power consuming physiologic sensors in rate adaptive pacemakers is unnecessary at such low levels of activity. Only when the activity level is such that an increased blood supply is needed to meet physiologic demand must the pacing device boost its stimulating rate above the lower rate limit. Then, too, until the level of activity reaches a further threshold does it become necessary to provide an increased level of power dissipation in the execution of a blended algorithm where multiple sensors have their outputs combined to produce control signals to the microprocessor for effecting an appropriate rate response.

In an article entitled "Left Ventricular Pacing Alters Cardiac Function During Exercise Compared with Bi-Ventricular Pacing: A Mid-term Prospective Study By Using a Hemodynamic Sensor", *PACE*, Vol. 24, April 2002, Part II, the authors concluded that for low levels of activity, bi-ventricular pacing, which is more power consuming than only left ventricular pacing, is no more beneficial to the patient than left ventricular pacing. However, they also concluded that during maximal and daily-life exercises, left ventricular pacing exhibited a higher incidence of arrhythmic events and lower performance as compared to bi-ventricular pacing and that, consequently, left ventricular pacing-induced interventricular dyssynchronization might impair left ventricular function on exercise. In accordance with a further feature of my invention, to both conserve battery power and to provide improved patient outcomes, the present invention provides a way of switching from left ventricular pacing to bi-ventricular pacing based upon the output of an activity sensor.

It is accordingly the principal object of the invention to provide increased longevity for implantable medical devices, such as pacemakers and pacemaker/defibrillators that provide rate responsive pacing based upon levels of activity determined through the use of multiple sensors by only activating the plural sensors when physiologic demand reaches a prescribed threshold.

A further object of the invention is to reduce the power consumption of activity sensors used in rate adaptive pacemakers and pacemaker/defibrillators while still providing rate response based on activity.

Yet another object of the invention is to provide an implantable medical device capable of automatically switching to a particular operating mode only when a predetermined level of activity has been reached.

SUMMARY OF THE INVENTION

The foregoing features, objects and advantages of the present invention result from an improved method for extending the battery life of an implantable medical stimulator, such as a cardiac pacemaker or an automatic implantable cardiac defibrillator, by first providing an implantable device having a stimulation pulse generator, a microprocessor-based controller for receiving input signals relating to a sensed physiologic parameter and providing control signals to the stimulation pulse generator, at least one additional power consuming feature and a battery power supply coupled to provide electrical energy to the stimulation pulse generator, the microprocessor-based controller and selectively to the additional power consuming feature. The device is implanted in a patient and a first physiologic sensor is used to sense a physiologic parameter that varies in relation to the level of the patient's physical activity. A determination is then made whether the sensed parameter falls into a prescribed range or possibly exceeds a predetermined threshold. If so, the additional power-consuming feature is enabled. Thus, so long as the patient remains relatively inactive, no power is consumed by the power consuming feature, be it additional physiologic sensors, or a change to a different operational mode exhibiting an increase in power consumption. In the case of a cardiac rhythm management device, if the patient exhibits some measure of chronotropic competence at relativity low levels of activity, but is chronotropically incompetent at higher levels of physical activity, the implanted device may be switched to a rate adaptive mode only when the patient's intrinsic rate reaches a crossover point where chronotropic incompetence sets in. In this fashion, battery power need only be delivered to the physiologic sensor or sensors when the cross-over point is reached.

The invention also contemplates that battery power can be conserved by switching to higher power-consuming modes only if dictated by a particular level of activity. For example, an implantable bradycardia pacer may be programmed to operate in, say, a DDD mode with the patient at rest or engaged in other low level activities, but automatically switch to a DDDR mode when a sensor determines that activity has exceeded a preset threshold.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF A PREFERRED EMBODIMENT

Figure 1:
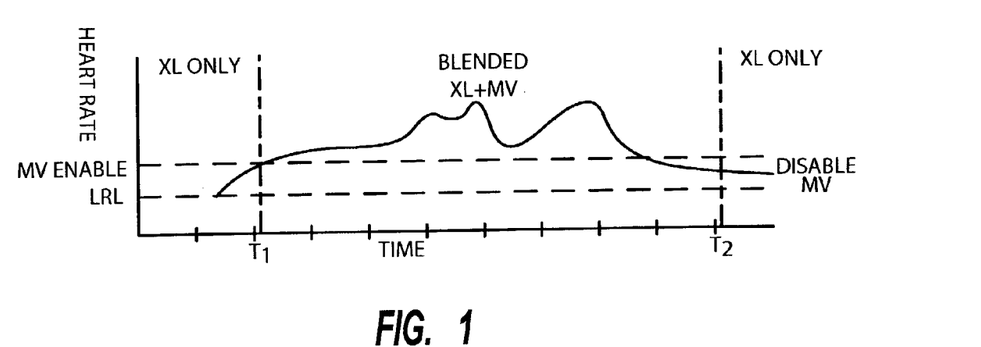
FIG. 1 is a plot of patient activity versus time showing for low levels of activity a single activity sensor and for higher levels of activity multiple sensors.

Referring first to FIG. 1, there is shown a plot of patient activity as measured by an accelerometer (XL) plotted against time as a level of exercise first increases and then subsequently decreases. Initially, with the patient at rest, the implanted cardiac stimulator will typically be pacing the patient's heart at a programmed lower rate limit (LRL). When the output from the accelerometer exceeds a threshold as at time, $T_1$, power is applied to the device's minute ventilation sensing circuitry, at which point the control signal developed for modifying the pacing rate becomes a blend of the output from the accelerometer and an output from the minute ventilation sensor. Once the pacing rate drops below a second threshold at time, $T_2$, the minute ventilation sensor is disabled (powered down) and, again, only the accelerometer is providing the rate controlling signal for the device's stimulating pulse generator. Thus, battery power is conserved so long as the patient's level of activity remains below the program threshold at which minute ventilation sensing kicks in.

Figure 2:
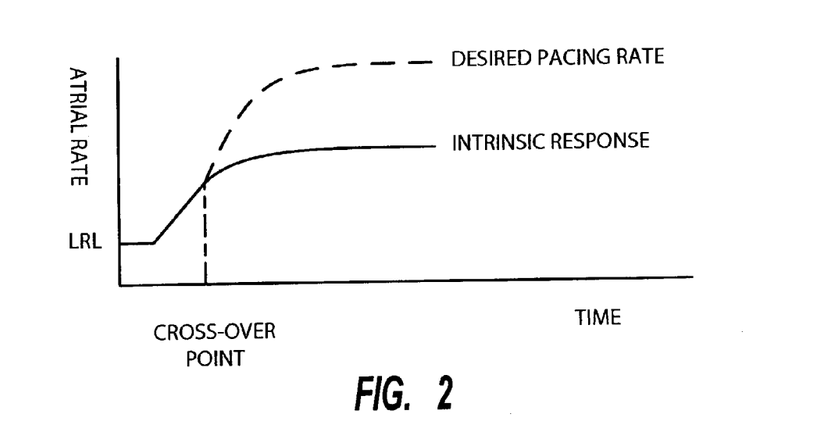
FIG. 2 is a plot of patient activity versus time showing that rate adaptive pacing may only be required when physical activity exceeds a level where intrinsic cardiac performance can no longer provide a required blood supply.

FIG. 2 is a plot of a patient's atrial rate versus time as physical activity increases and then decreases where such patient suffers from chronotropic incompetence. In many patients, the heart's natural pacemaker (its sinus node) produces intrinsic cardiac depolarization at an appropriate rate when resting or engaged in low activity efforts. However, as physical activity increases, a point is reached where cardiac output no longer increases with activity and, in this event, rate adaptive pacing is in order. Thus, in accordance with the method of the present invention, the physiologic sensor, which is a power-consuming device, remains dormant so long as intrinsic cardiac activity is sufficient to satisfy physiologic demand. Only when the cross-over point shown in FIG. 2 is reached, is power applied to the physiologic sensor that is used to develop a Delta rate control signal for the device's microprocessor-based controller that is used to control the device's stimulating pulse generator.

Figure 3:
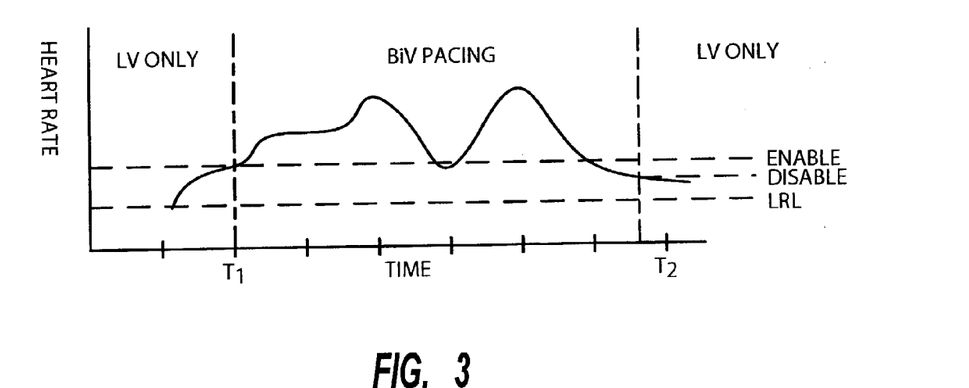
FIG. 3 is a plot of activity vs. mode of pacing.

FIG. 3 is a plot of heart rate over time with varying rates of patient activity. With the patient at rest, heart rate may be at the lower rate limit (LRL) where the pacing mode is to stimulate only the left ventricle. As activity increases, a point is reached at $T_1$ where a predetermined programmed threshold is exceeded whereupon the pacing mode automatically switches to biventricular pacing. The device stays in this mode until time $T_2$ where because of a decrease in physical activity, the heart rate has dropped below a second predetermined threshold whereupon biventricular pacing ceases and only left ventricular pacing takes place.

Figure 4:
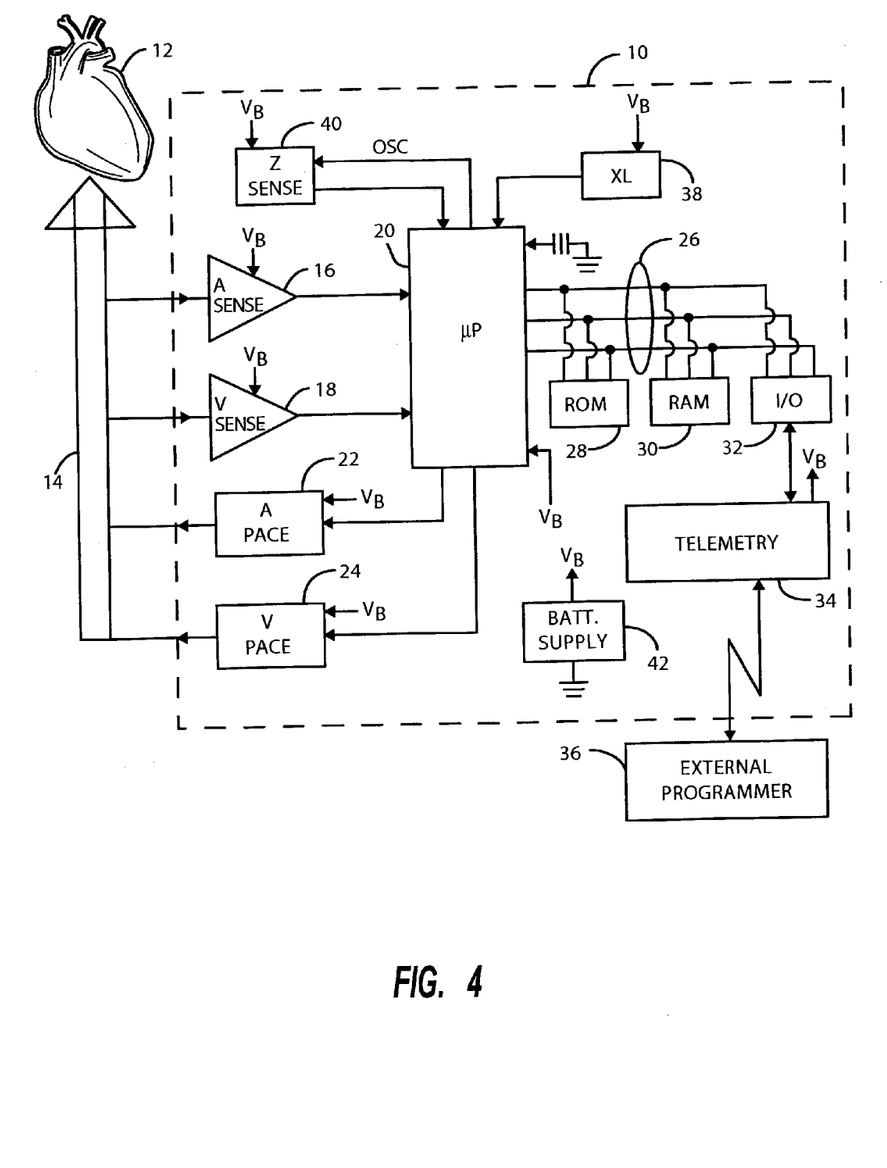
FIG. 4 is a block diagram of an implantable cardiac rhythm management device in which the method of the present invention finds application.

For a better understanding of the invention, FIG. 4 is included to illustrate the essential components of an implantable medical stimulating device, namely, an implantable pacemaker in which the power conserving method of the present invention is carried out.

The implantable pacemaker is shown as being enclosed by the broken line box 10 and is adapted to be connected to a patient's heart 12 by means of one or more pacing leads 14. As is well known in the art, a pacing lead is used to deliver stimulating pulses from the device 10 to the heart and to apply signals relating to cardiac depolarization originating in the heart to the device 10.

Included within the implantable device 10 is an atrial sense amplifier 16 and a ventricular sense amplifier 18. The atrial sense amplifier detects, amplifies and shapes atrial depolarization signals (P-waves) and the ventricular sense amplifier detects, amplifies and shapes ventricular depolarization signals (R-waves). The outputs from the atrial sense amplifier 16 and ventricular sense amplifier 18 are applied to a microprocessor-based controller 20. The microprocessor-based controller is programmed to operate in a selected mode to apply control signals to an atrial pace pulse generator 22 and a ventricular pace pulse generator 24 for controlling the amplitude and time of delivery of cardiac stimulating pulses to the heart, via the lead 14.

The microprocessor-based controller 20 includes a microprocessor therein that has a bus 26 for providing address, control and data signals to a ROM 28, a RAM 30 and an input/output interface device 32. The program executed in the microprocessor for controlling the pulse generators 22 and 24 will typically be stored in the ROM 28. Operands used in the execution of the programs and data relating to a variety of other events are stored in the RAM memory 28.

The I/O interface 32 controls a telemetry circuit 34 whereby information developed and stored in the memory 30 may be delivered transcutaneously to an external programmer/monitor 36. The external programmer may also send programmable parameters and other information back to the RAM memory 30 by way of the telemetry circuit 34 and the I/O interface 32.

In a rate adaptive device, one or more physiologic sensors, over and above the atrial sense amplifier 16 and the ventricular sense amplifier 18, may also be incorporated whereby the microprocessor-based controller can alter the rate at which cardiac stimulating pulses are delivered by the pulse generators 22 and 24 based upon changing levels of physiologic demand. In FIG. 4, the additional physiologic sensors include an accelerometer (XL) 38 and an impedance sensing circuit 40. They should be considered as exemplary only since a variety of other physiologic sensors known in the art may be used as well. As is explained in U.S. Pat. No. 4,567,892 to Plicchi et al. and in U.S. Pat. No. 4,901,725 to Nappholz et al., the output from the impedance sensing circuit varies in accordance with respiratory activity and is proportional to a patient's minute ventilation (MV). As is explained in those patents, a radio frequency oscillator delivers a radio frequency carrier signal between spaced electrodes in the heart and this carrier or drive signal becomes modulated, not only by the beating action of the heart as blood flows in and out of an involved cardiac chamber, but also an artifact due to breathing can be detected in the modulation envelope and isolated using known signal processing techniques implemented in the microprocessor 20.

Also shown in the block diagram representation of an implantable cardiac pacer illustrated in FIG. 4 is a battery supply 42 that is used to provide the requisite operating voltages to the several circuits comprising the pacemaker. In that in a rate responsive pacer, the physiologic sensors 38 and 40 are only required upon a patient reaching a certain level of physical activity, power is conserved and battery life will be prolonged if the sensors 38 and 40 remain disabled so long as the patient's physiologic demand is satisfied.

Figure 5:
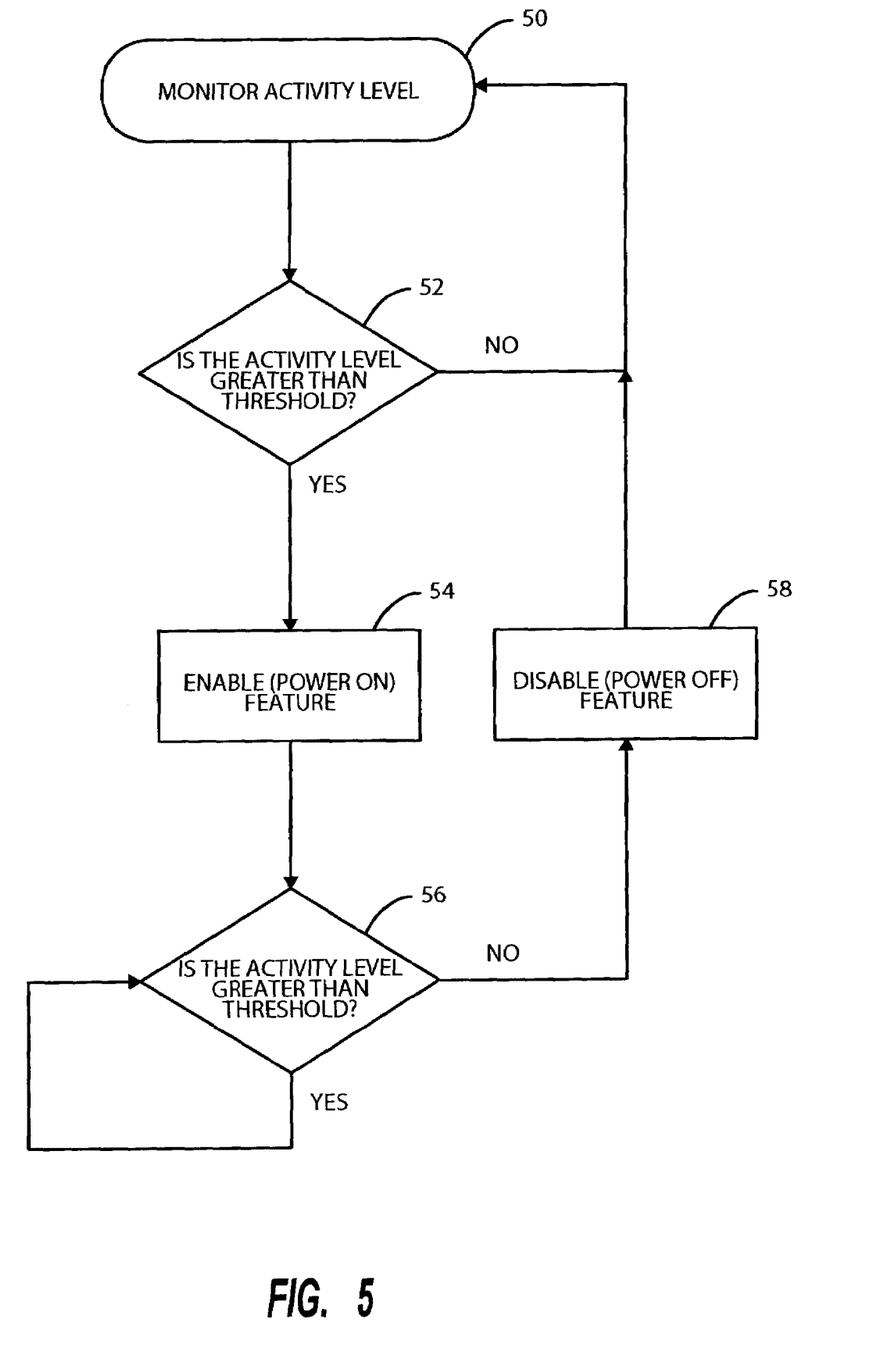
FIG. 5 is a software flow diagram of a basic algorithm implementing the method of the present invention.

FIG. 5 is a software flow diagram of the basic algorithm executed by the microprocessor-based controller 20 for conserving battery power in an implantable, rate-responsive cardiac stimulator. The output from the accelerometer 38 or heart rate derived from the output of the sensors 16 or 18 or other means to determine activity, may be used as a measure of activity level as represented by block 50 in FIG. 5. A test is made at decision block 52 to determine whether the activity level is greater than a predetermined threshold level and, if not, the software loops back to block 50. If the test at decision block 52 indicates that the activity level is above the preset threshold, then power is delivered from the battery 42 to a power consuming component or feature, such as the MV sensing circuitry 40, so that its output can be blended with the XL output in creating a Delta rate control signal for the stimulating pulse generators 22 and 24. This operation is represented by block 54 in FIG. 5. A test is then continuously made to determine whether the activity level has remained greater than the preset threshold (decision block 56) and, if so, the MV sensor circuitry 40 remains powered up. If the activity level again falls below the set threshold, the power to the MV sensor 40 is turned off (block 58) and control returns to the monitoring step 50.

As previously indicated, the mechanism for monitoring activity level may be any one of the following or any combination thereof: heart rate sensor, accelerometer, minute ventilation sensor, posture sensor, blood pressure sensor, blood temperature sensor, blood oxygen saturation, etc. Likewise, the feature enabled and disabled could be any of the following: a rate response pacing algorithm, a blended sensor rate response pacing algorithm, pacing delivery therapy, arrhythmia discrimination, any other power-use intensive feature that can be disabled during periods of low activity. Pacing delivery therapy may involve either pacing of one ventricular chamber when activity is low or both chambers essentially simultaneously, i.e., bi-ventricular pacing when physical activity is higher.

Figure 6:
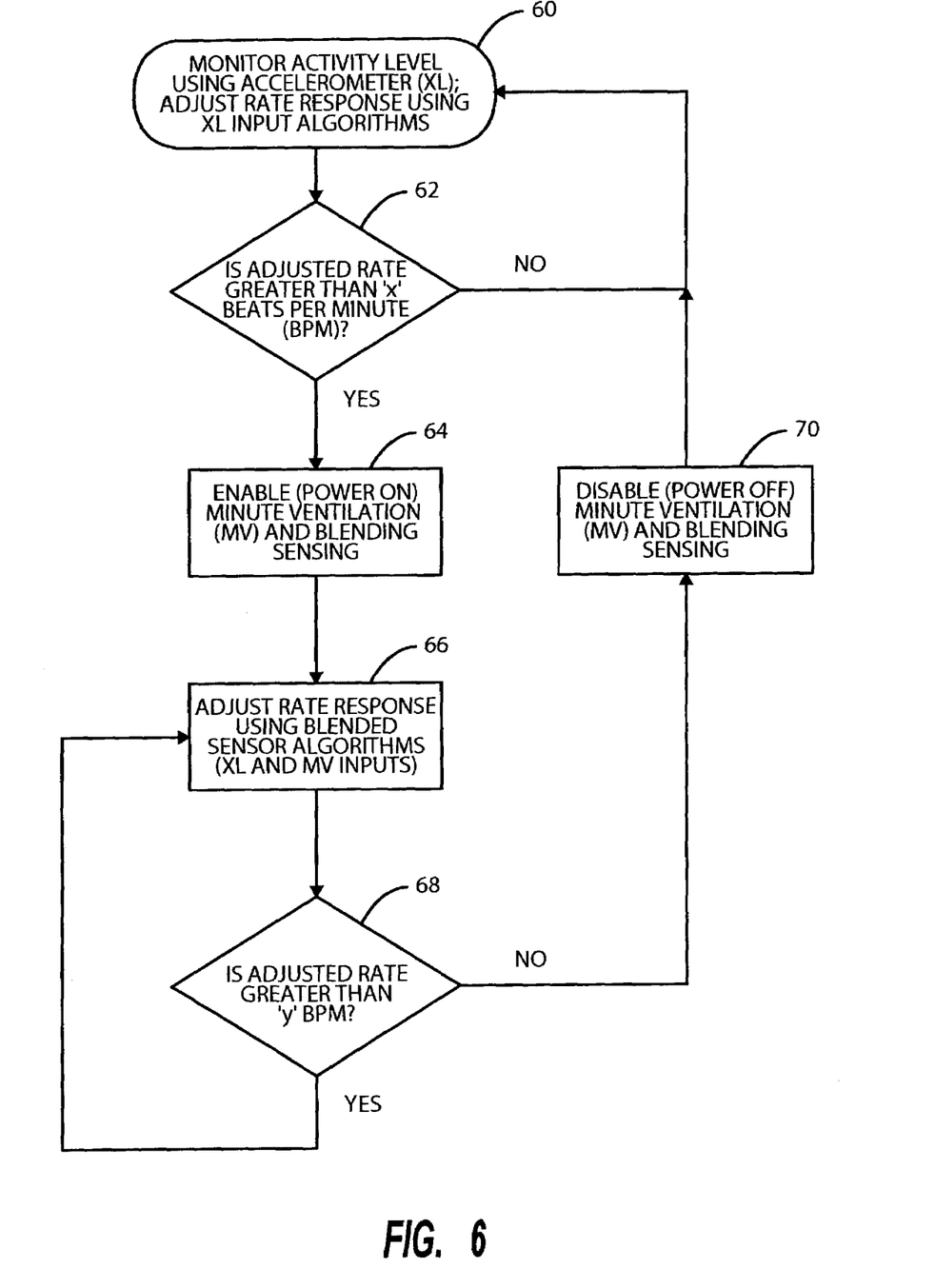
FIG. 6 is a software flow diagram of an algorithm for battery conservation where activity levels are monitored by an accelerometer and used to enable minute ventilation to be blended in arriving at a Delta rate signal for a rate adaptive cardiac stimulator.

Turning next to FIG. 6, there is illustrated a software flow diagram of an algorithm in which patient activity, as measured by an accelerometer (XL) is used to enable or disable multi-sensor blending in a rate responsive cardiac pacemaker. In this algorithm, activity levels, as monitored by an accelerometer, enable minute ventilation and blended sensing only when a threshold of activity is exceeded to thereby conserve battery power. As indicated by operation block 60, activity level is monitored using the accelerometer 38 and the rate response is adjusted accordingly relative to a programmed LRL. A test is made at decision block 62 to determine whether the adjusted rate is greater than a predetermined number (x) of beats-per-minute and, if so, the MV sensing circuitry 40 is powered on (block 64). Moreover, when that threshold is exceeded, the microprocessor-based controller may be made to execute a suitable blending algorithm whereby the outputs from both the MV sensing circuitry 40 and the XL 38 are used in establishing the Delta pace rate for the microprocessor-controlled stimulating pulse generators 22 and/or 24.

At block 66, the Delta rate control signal is computed and then a test is made at decision block 68 to determine whether the blended rate is greater than a second threshold of (y) beats-per-minute. If the Delta rate drops below the "y" threshold, power to the MV sensing circuitry 40 is turned off and the blending algorithm executed by the microprocessor is disabled (block 70). By providing two thresholds, x and y, hysteresis is added into the algorithm. It is of interest to note here that the first decision at block 62 uses the response based on the output of the accelerometer while the second decision at block 68 may use the response based on the output of the accelerometer, or the response based on the output of the MV sensor or the response based on a combination of both of those sensors.

Figure 7:
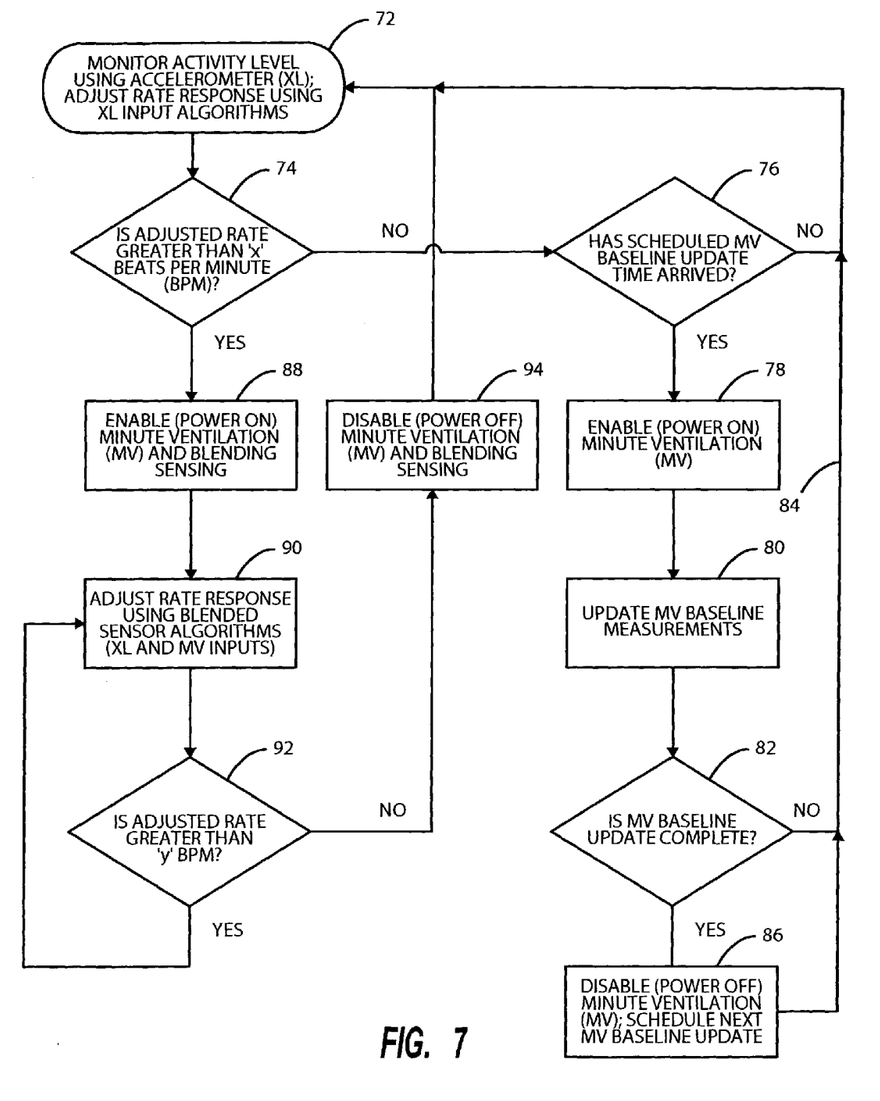
FIG. 7 is a software flow chart adding minute ventilation baseline update to the algorithm of FIG. 6.

Turning next to the algorithm represented by the flow chart of FIG. 7, updating of the MV sensor baseline is provided for. The MV baseline is a unique value for each patient. It is the resting minute ventilation from which the Delta MV is computed during times of activity in order to determine the appropriate pacing rate. Baseline respiratory may change over time due to changes in a patient's physiology and also possibly due to maturation of the lead interface that the MV sensor utilizes.

At operation block 72, activity level is monitored using the XL 38 and the pacing rate is adjusted from a lower rate limit value based upon the XL sensed activity. A test is made at decision block 74 to determine whether the adjusted rate has reached a first predetermined threshold (x beats-per-minute). If not, a further test is made at decision block 76 to determine whether a time has come where the MV baseline should be updated. If the elapsed time between baseline updates has expired, power is applied to the MV circuitry 40 (block 78) and the MV baseline is updated (block 80). At decision block 82, the algorithm tests whether the baseline update procedure has been completed and, if not, control loops back over path 84 to the activity monitoring operation 72. If the test at decision block 82 has indicated that the baseline update procedure has been completed, the MV sensor 40 is again disabled and the subsequent update time is established (block 86).

If the test at decision block 74 indicates that the accelerometer modified rate response exceeds the threshold of "x" beats-per-minute, the MV sensing circuitry 40 is enabled, as is the blending algorithm utilized by the microprocessor 20. These operations are represented by block 88 in FIG. 7. At block 90, the algorithm is operative to adjust the Delta pacing rate of the pulse generators 22 and/or 24 using a blended combination of the XL and MV sensor outputs. At decision block 92, a determination is made whether the pacing rate, as adjusted by the blended output, exceeds a second threshold, "y" beats-per-minute. If the patient's physiologic demand has dropped so that the adjusted rate is no longer greater than the threshold, the MV sensor 40 is disabled, as is the blended sensing algorithm employed (block 94).

Figure 8:
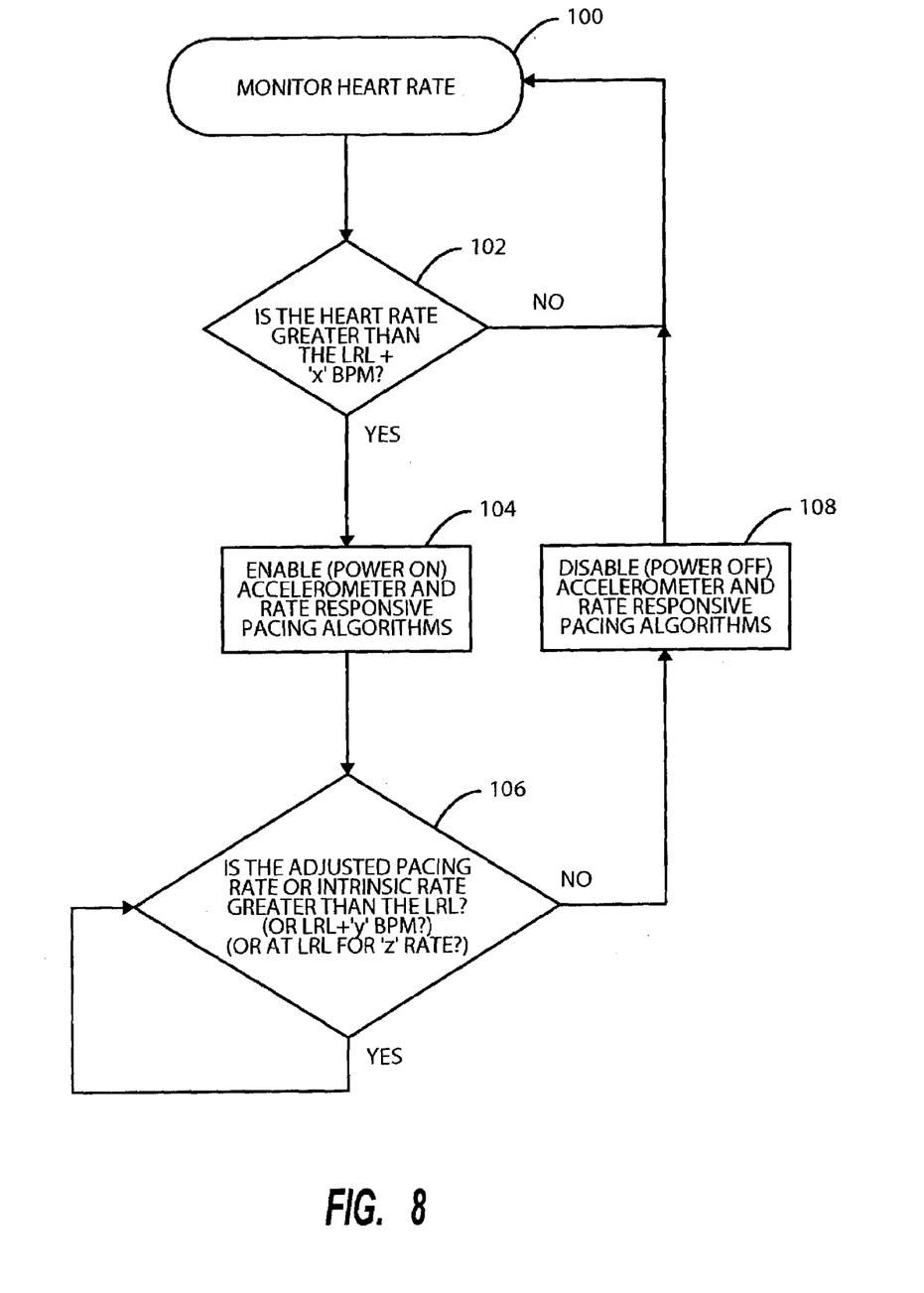
FIG. 8 is a software flow chart for implementing power conservation in cardiac stimulators for addressing chronotrophic incompetence.

Turning next to algorithm represented by the flow chart of FIG. 8, it illustrates the implementation of battery power conservation in a rate responsive cardiac rhythm management device for use with patient's exhibiting chronotropic incompetence. The overall concept illustrated in FIG. 8 is that the pacing mode of the implantable device is made to switch to its rate-responsive mode (DDD-to-DDDR) at a defined level above the lower rate limit and reverts back to a non-rate responsive mode (DDDR-to-DDD) when the paced rate or intrinsic rate falls below another defined level. As is represented by block 100, the microprocessor-based controller 20 utilizes the output from the ventricular sense amplifier 18 to determine heart rate. So long as the heart rate remains below a programmed level (LRL+"X"BPM) the device remains in its non-rate responsive state. However, when the test at decision block 102 indicates that the patient's intrinsic or paced heart rate is above the indicated threshold, the device switches to the DDDR mode as indicated by operation block 104 in FIG. 8.

As is reflected by the decision block 106, the device will remain in the rate responsive mode until it is detected that the rate adjusted pacing rate or intrinsic rate falls below a second threshold, LRL+"Y" beats per minute where Y is less than X. When this happens, the device is switched to its non-rate responsive mode which, of course, requires less battery power than the rate responsive mode. See block 108.

Rather than testing whether the rate adjusted pacing rate or intrinsic rate is less than a predetermined threshold, it is also contemplated that the switch-over to non-rate adaptive pacing take place if and when the detected heart rate returns to the programmed lower rate limit for a predetermined time interval, "Z" seconds. See decision block 106.

Those skilled in the art can appreciate that the physician can simply input the LRL and the implanted device will automatically set up the ranges "X" and "Y". Alternatively, the physician can input the lower rate limit (LRL) and the offset thresholds for switching to and from a rate-responsive mode. In that the patient's heart rate spends the majority of the time in the non-rate-responsive zone, power savings are realized. This implementation provides adequate blood supply for patients with true chronotropic incompetence since the patient's cardiac output need only be supplemented through an increase in the pacing rate when the patient is engaged in higher levels of activity.

Figure 9:
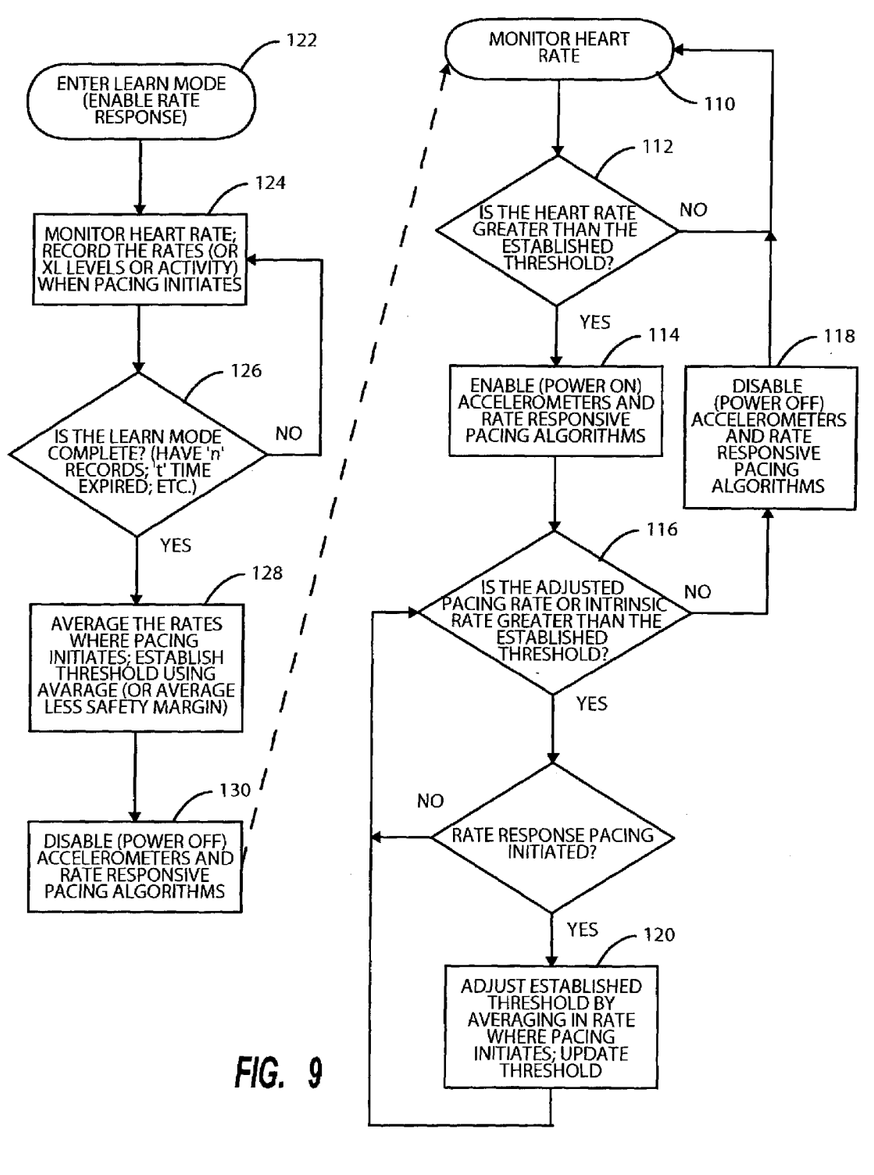
FIG. 9 is a software flow chart for power management having a self-learning capability.

FIG. 9 illustrates an algorithm which constitutes an enhancement of the algorithm of FIG. 8. It adds to the algorithm of FIG. 8 a learning capability whereby the thresholds at which mode switching takes place are self-adjusting. At operation block 110, the patient's heart rate is monitored and at decision block 112, the heart rate is tested to determine whether it is greater than an established threshold. Only if it is will the physiologic sensor (accelerometer 38) be powered up and the device's rate responsive pacing algorithm be executed. See operation block 114 in FIG. 9. While operating in the rate responsive mode, the adjusted pacing rate or the intrinsic heart rate is tested to determine whether it is greater than an established threshold (decision block 116) and, if not, the sensor 38 is powered off and execution of the rate responsive pacing algorithm is terminated (block 118).

Had the test at decision block 116 indicated that the intrinsic rate or the adjusted pacing rate is greater than the established threshold, and rate responsive pacing has been initiated, the established threshold may be adjusted by taking into account the average rate over time where pacing initiates (block 120). The software loop, that includes decision block 116 and operation block 120, functions to continually monitor and update the enabling threshold to provide a safety margin in cases where the level where the patient falls into incompetence worsens or improves over time.

To avoid the possibility that a threshold may initially be set too high, it has proven expedient to include the software routine to a left of the dashed line arrow leading to block 110 in FIG. 9. Here, the software operates in a learn mode by first enabling the rate response sensor 38 (block 122). The implantable device monitors the heart rate and the heart rate or accelerometer output is recorded in the RAM memory 30 at the time that pacing begins (block 124). This operation continues until a predetermined time set up for the "learn" mode has expired or, alternatively, a predetermined number, n, records have been stored. This test is made at decision block 126. Upon completion of the "learn" mode, the stored value of the rates where pacing began are averaged and used to establish the threshold above the LRL where rate adaptive pacing is initiated. See block 128. Once the threshold is established, the power to the accelerometer can be shut off and rate responsive pacing terminated as indicated by block 130.

Figure 10:
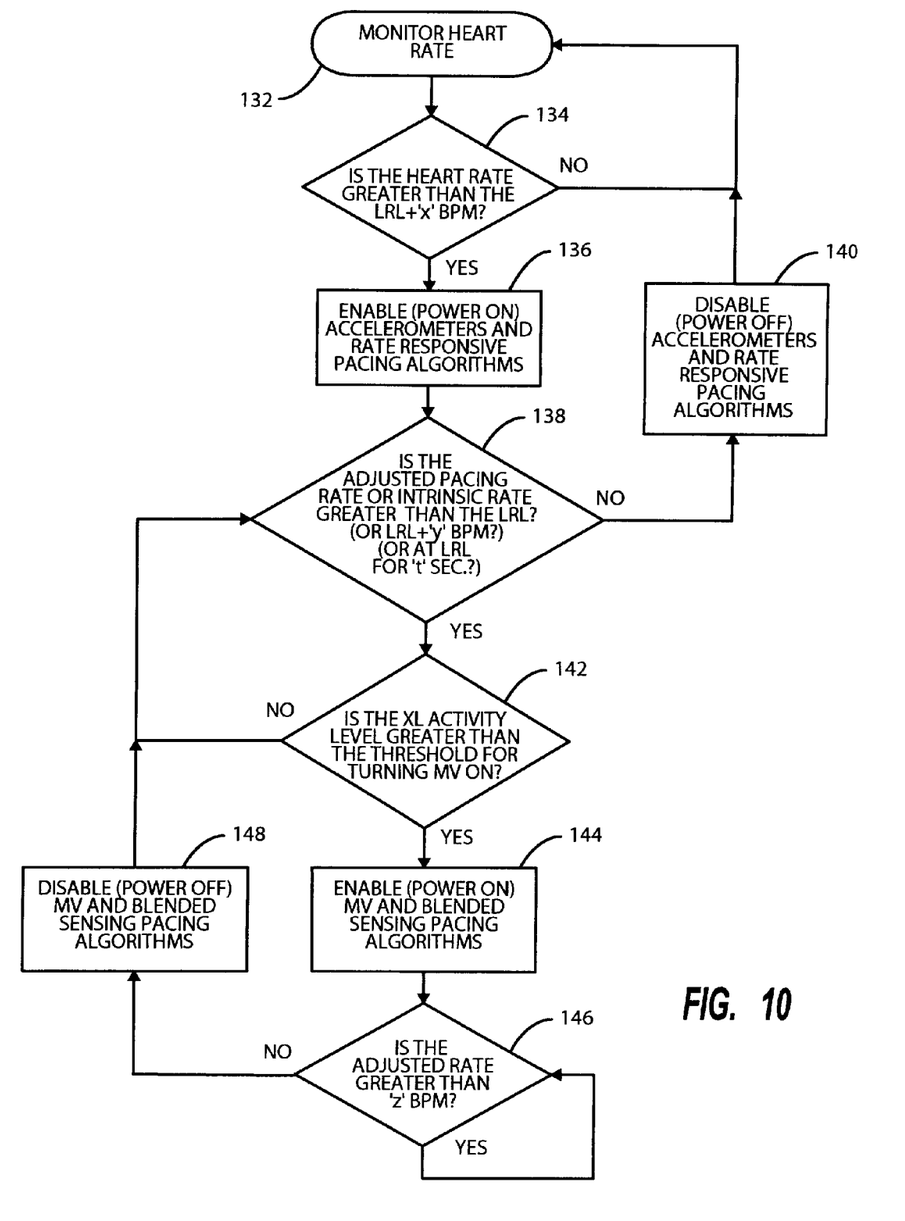
FIG. 10 is a software flow chart in which a first activity monitor enables a feature which, in turn, can enable a further feature.

FIG. 10 is a flow chart for an algorithm that may be implemented in the microprocessor-based controller 20 whereby a first activity monitor is used to enable a feature which, in turn, enables a further feature. More particularly, the flow chart of FIG. 10 is of an algorithm that permits the combining of chronotropic incompetence power management with blended sensor power management. Here, at block 132, heart rate derived from the ventricular depolarization signals picked up by the sense amplifier 18 is monitored and tested at decision block 134 to determine when the monitored rate exceeds a threshold level "X" above LRL. The value of X may be determined by execution of the learning mode steps shown to the left of the broken line arrow in FIG. 8. When that threshold is exceeded, the accelerometer 38 and its associated rate response pacing algorithm are enabled (block 136). Following that, a further test is made to determine whether either the adjusted pacing rate or the patient's intrinsic rate is greater than a predetermined value which may correspond either to the lower rate limit or to the lower rate limit plus a predetermined program threshold value or, alternatively, whether the adjusted pacing rate is at the lower rate limit for a predetermined amount of time. See decision block 138. If none of these conditions prevail, power to the accelerometer is turned off and the microprocessor ceases to execute the programmed rate responsive pacing algorithm involved (block 140). If the condition at decision block 138 is satisfied, another test is made at decision block 142 where it is determined whether the accelerometer output is greater than a threshold at which the minute ventilation sensor 40 is activated. When the condition is satisfied, the minute ventilation sensor 40 is powered on and the microprocessor-based controller 20 is made to execute the program for blending the accelerometer output and the minute ventilation output in creating a rate modifying signal for the pulse generator 24. Pacing then continues with the blended rate adjusting factor until the patient's activity is such that the adjusted rate falls below yet another threshold value that is programmed into the RAM memory of the device. This test is represented by decision block 146. When the condition there is no longer satisfied, power to the minute ventilation sensing circuitry 40 is discontinued and the microprocessor also discontinues the execution of the blended sensing pacing algorithms (block 148).

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself For example, it is possible that a power-consuming feature, such as a sleep apnea treatment, need only be powered during periods of relative inactivity. Thus, instead of turning on a device when measured activity goes into a range above a prescribed threshold, it is also contemplated that a power consuming feature can be powered up only when a level of physical activity is in a range below a set threshold.

The invention claimed is:

1. A method for extending the battery life of an implantable cardiac rhythm management device, comprising the steps of:
 a) providing a cardiac rhythm management device having a stimulation pulse generator, a microprocessor-based controller adapted to receive input signals relating to depolarization of at least one cardiac chamber and for providing control signals to the stimulation pulse generator, at least one additional power consuming feature, and a battery power supply coupled to provide electrical energy to the stimulation pulse generator, the microprocessor-based controller and selectively to the additional power consuming feature;
 b) implanting the cardiac rhythm management device in a patient;
 c) sensing the patient's heart rate;
 d) determining when the sensed heart rate ceases to increase sufficiently to accommodate further increase in activity level by averaging the heart rate values where pacing initiates over a predetermined time interval during which patient activity level repeatedly varies between an at rest state and a moderately active state;
 e) initiating execution of a programmed rate response algorithm by the microprocessor-based controller.

2. The method of claim 1 and further including the step of:
 switching back to execution of a non-rate response algorithm by the microprocessor-based controller when a patient's sensed heart rate is sufficient to accommodate a current level of activity.

3. A method for extending the battery life of an implantable cardiac rhythm management device, comprising the steps of:
 a) providing a cardiac rhythm management device having a stimulation pulse generator, a microprocessor-based controller adapted to receive input signals relating to depolarization of at least one cardiac chamber and for providing control signals to the stimulation pulse generator, at least one additional power consuming feature, and a battery power supply coupled to provide electrical energy to the stimulation pulse generator, the microprocessor-based controller and selectively to the additional power consuming feature;
 b) implanting the cardiac rhythm management device in a patient;

c) sensing a patient's intrinsic heart rate that varies in relation to the level of a patient's physical activity with a first physiologic sensor;

d) determining whether or not the sensed physiologic parameter is within a predetermined range above a point where the intrinsic heart rate exhibits chronotropic incompetence; and e) enabling the at least one additional power consuming feature only if the sensed parameter is within said predetermined range.

4. The method as in claim 3 and further including the step of disabling the at least one additional power consuming feature following the enabling thereof when the sensed parameter falls outside of said predetermined range.

5. The method as in claim 3 and further including the step of disabling the at least one additional power consuming feature following the enabling thereof a predetermined time after a time when the sensed parameter falls within of said predetermined range.

6. The method as in claim 3 wherein the additional power consuming feature comprises a second physiologic sensor.

7. The method of claim 6 wherein the first physiologic sensor senses movement of the patient and the second physiologic sensor measures the patient's minute ventilation.

8. The method as in claim 7 wherein the first physiologic sensor comprises an accelerometer.

9. The method as in claim 3 wherein the predetermined range is below the point where the intrinsic heart rate exhibits chronotropic incompetence by a predetermined safety margin.

10. The method as in claim 3 wherein the first physiologic sensor is an activity sensor and the additional power consuming feature is execution of a rate response pacing algorithm.

11. The method as in claim 3 wherein the first physiologic sensor is a patient posture sensor and the additional power consuming feature is execution of a rate response pacing algorithm.

12. The method as in either claim 10 or claim 11 wherein the rate response pacing algorithm is a blended sensor rate response pacing algorithm.

13. The method as in claim 3 wherein the one additional power consuming feature is delivery of bi-ventricular pacing pulses by the stimulation pulse generator.

14. A method for extending the battery life of an implantable cardiac rhythm management device, comprising the steps of:

a) providing a cardiac rhythm management device having a stimulation pulse generator, a microprocessor-based controller adapted to receive input signals relating to depolarization of at least one cardiac chamber and for providing control signals to the stimulation pulse generator, at least one additional power consuming feature comprising delivery of bi-ventricular pacing pulses by the stimulation pulse generator, and a battery power supply coupled to provide electrical energy to the stimulation pulse generator, the microprocessor-based controller and selectively to the additional power consuming feature;

b) implanting the cardiac rhythm management device in a patient;

c) sensing a first physiologic parameter that varies in relation to the level of a patient's physical activity with a first physiologic sensor;

d) determining whether the sensed physiologic parameter is within a predetermined range; and e) enabling the at least one additional power consuming feature only if the sensed parameter is within said predetermined range.

15. The method as in claim 14 and further including the step of disabling the at least one additional power consuming feature following the enabling thereof when the sensed parameter falls outside of said predetermined range.

16. The method as in claim 14 and further including the step of disabling the at least one additional power consuming feature following the enabling thereof a predetermined time after a time when the sensed parameter falls outside of said predetermined range.

17. The method as in claim 14 wherein the additional power consuming feature comprises a second physiologic sensor.

18. The method of claim 17 wherein the first physiologic sensor senses movement of the patient and the second physiologic sensor measures the patient's minute ventilation.

19. The method as in claim 18 wherein the first physiologic sensor comprises an accelerometer.

20. The method as in claim 14 wherein the first physiologic parameter comprises the patient's intrinsic heart rate and the predetermined range is below a point where the intrinsic heart rate exhibits chronotropic incompetence.

21. The method as in claim 20 wherein the predetermined range is below the point where the intrinsic heart rate exhibits chronotropic incompetence by a predetermined safety margin.

22. The method as in claim 14 wherein the first physiologic sensor is an activity sensor and the additional power consuming feature is execution of a rate response pacing algorithm.

23. The method as in claim 14 wherein the first physiologic sensor is a patient posture sensor and the additional power consuming feature is execution of a rate response pacing algorithm.

24. The method as in either claim 22 or claim 23 wherein the rate response pacing algorithm is a blended sensor rate response pacing algorithm.

25. A method for extending the battery life of an implantable cardiac rhythm management device, comprising the steps of:

a) providing a cardiac rhythm management device having a stimulation pulse generator, a microprocessor-based controller adapted to receive input signals relating to depolarization of at least one cardiac chamber and for providing control signals to the stimulation pulse generator, a sleep apnea therapy device, and a battery power supply coupled to provide electrical energy to the stimulation pulse generator, the microprocessor-based controller and selectively to the sleep apnea therapy device;

b) implanting the cardiac rhythm management device in a patient;

c) sensing body motion that varies in relation to the level of a patient's physical activity with a first physiologic sensor;

d) determining whether the body motion is within a predetermined range; and e) enabling the sleep apnea therapy device only if the body motion is within said predetermined range.

26. The method as in claim 25 and further including the step of disabling the sleep apnea therapy device following the enabling thereof when the sensed body motion falls outside of said predetermined range.

27. The method as in claim 25 and further including the step of disabling the sleep apnea therapy device following the enabling thereof a predetermined time after a time when the sensed body motion falls outside of said predetermined range.

28. The method as in claim 25 wherein the additional power consuming feature comprises a second physiologic sensor.

29. The method of claim 28 wherein the first physiologic sensor senses movement of the patient and the second physiologic sensor measures the patient's minute ventilation.

30. The method as in claim 29 wherein the first physiologic sensor comprises an accelerometer.

31. The method as in claim 25 wherein the first physiologic sensor is an activity sensor and the additional power consuming feature is a sleep apnea therapy device.

* * * * *